United States Patent
Lagrange et al.

(10) Patent No.: US 9,993,411 B2
(45) Date of Patent: *Jun. 12, 2018

(54) DYE COMPOSITION USING A PHENOL-DERIVED COUPLER IN A MEDIUM RICH IN FATTY SUBSTANCES, PROCESSES AND DEVICES

(71) Applicant: L'OREAL, Paris (FR)

(72) Inventors: Alain Lagrange, Coupvray (FR); Marie Mignon, Paris (FR)

(73) Assignee: L'OREAL, Paris (FR)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/314,283

(22) Filed: Jun. 25, 2014

(65) Prior Publication Data

US 2014/0366284 A1    Dec. 18, 2014

Related U.S. Application Data

(63) Continuation of application No. 14/114,555, filed as application No. PCT/EP2012/057206 on Apr. 19, 2012, now abandoned.

(Continued)

(30) Foreign Application Priority Data

Apr. 29, 2011  (FR) ...................... 11 53704

(51) Int. Cl.
*A61Q 5/10* (2006.01)
*A61K 8/49* (2006.01)
(Continued)

(52) U.S. Cl.
CPC .............. *A61K 8/498* (2013.01); *A45D 19/02* (2013.01); *A61K 8/22* (2013.01); *A61K 8/347* (2013.01);
(Continued)

(58) Field of Classification Search
CPC . A61Q 5/10; A61K 8/22; A61K 8/347; A61K 8/49
(Continued)

(56) References Cited

U.S. PATENT DOCUMENTS

| | | | |
|---|---|---|---|
| 4,003,699 A | 1/1977 | Rose et al. | |
| 4,104,020 A * | 8/1978 | Rose ...................... | A61K 8/494 548/361.1 |
| 4,137,180 A | 1/1979 | Naik et al. | |
| RE30,199 E | 1/1980 | Rose et al. | |
| 4,874,554 A | 10/1989 | Lange et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Lowe et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 8,070,831 B2 | 12/2011 | Simonet et al. | |
| 2002/0050013 A1 | 5/2002 | Vidal et al. | |
| 2003/0019051 A9 | 1/2003 | Vidal et al. | |

(Continued)

FOREIGN PATENT DOCUMENTS

| | | | |
|---|---|---|---|
| DE | 2357215 A1 | 5/1975 | |
| DE | 2359399 A1 | 6/1975 | |

(Continued)

OTHER PUBLICATIONS

STIC Search Report dated Oct. 14, 2014.*

(Continued)

*Primary Examiner* — Eisa B Elhilo
(74) *Attorney, Agent, or Firm* — The Marbury Law Group, PLLC

(57) ABSTRACT

The present invention relates to a composition for dyeing keratin fibres, comprising: at least one fatty substance, at least one surfactant; at least one oxidation base, at least one coupler of formula (B3) below and also salts thereof, optical and geometrical isomers and tautomers thereof, and hydrates thereof: (B3) in which; $R^1$, $R^3$, $R^5$ represent a hydrogen; a $C_1$-$C_8$ alkyl or alkenyl, —SR or —OR; a ($C_1$-$C_4$)alkylcarbonyl; hydrocarbonyl; sulphonic or carboxylic acid; $R^2$, $R^4$ represent a hydrogen, a $C_1$-$C_8$ alkyl or alkenyl; —OR'; two groups chosen from $R^1$, $R^2$, $R^3$, $R^4$, $R^5$ and borne by adjacent carbon atoms may form, together with said carbon atoms, a ring or a heterocycle which is optionally substituted, and which is optionally interrupted with one or more carbonyl groups; at least one of the radicals $R^1$, $R^3$, $R^5$ representing a hydrogen; at least one of the radicals $R^2$ or $R^4$ denoting a group —OR' with R' representing a $C_1$-$C_8$ alkyl or alkenyl, it being possible for this radical to form, with the carbon atom bearing it, one of the neighbouring carbon atoms and its substituent, a heterocycle; at least one alkalinizing agent; the fatty substance content representing in total at least 25% by weight relative to the total weight of the composition. The present invention also relates to a process using this composition in the presence of at least one chemical oxidizing agent, and to multicompartment devices suitable for the implementation of the invention.

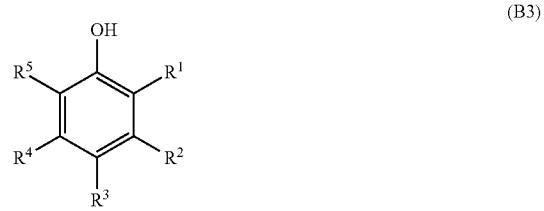

(B3)

18 Claims, No Drawings

Related U.S. Application Data

(60) Provisional application No. 61/483,317, filed on May 6, 2011.

(51) Int. Cl.
*A61K 8/34* (2006.01)
*A61K 8/35* (2006.01)
*A61K 8/368* (2006.01)
*A45D 19/02* (2006.01)
*A61K 8/22* (2006.01)
*A61K 8/365* (2006.01)
*A61K 8/41* (2006.01)
*A61K 8/92* (2006.01)

(52) U.S. Cl.
CPC ............... *A61K 8/35* (2013.01); *A61K 8/365* (2013.01); *A61K 8/368* (2013.01); *A61K 8/41* (2013.01); *A61K 8/4973* (2013.01); *A61K 8/92* (2013.01); *A61Q 5/10* (2013.01); *A61K 2800/591* (2013.01)

(58) Field of Classification Search
USPC .......................................................... 8/405
See application file for complete search history.

(56) References Cited

U.S. PATENT DOCUMENTS

| | | | |
|---|---|---|---|
| 2005/0144740 A1* | 7/2005 | Gross | A61K 8/35 8/405 |
| 2006/0265818 A1* | 11/2006 | Seiler et al. | 8/412 |
| 2010/0154140 A1* | 6/2010 | Simonet et al. | 8/416 |
| 2010/0247465 A1 | 9/2010 | Simonet et al. | |

FOREIGN PATENT DOCUMENTS

| | | | |
|---|---|---|---|
| DE | 3843892 | A1 | 6/1990 |
| DE | 4133957 | A1 | 4/1993 |
| DE | 19543988 | A1 | 5/1997 |
| EP | 0004366 | A2 | 10/1979 |
| EP | 0770375 | A1 | 5/1997 |
| FR | 2733749 | A1 | 11/1996 |
| FR | 2801308 | A1 | 5/2001 |
| FR | 2886136 | A1 | 12/2006 |
| FR | 2946875 | A1 | 12/2010 |
| GB | 1026978 | A | 4/1966 |
| GB | 1153196 | A | 5/1969 |
| GB | 1572983 | A | 8/1980 |
| JP | 02019576 | | 1/1990 |
| JP | 05163124 | | 6/1993 |
| WO | 9408969 | A1 | 4/1994 |
| WO | 9408970 | A1 | 4/1994 |
| WO | 9615756 | A1 | 5/1996 |
| WO | 2010070244 | A2 | 6/2010 |

OTHER PUBLICATIONS

International Search Report for PCT/EP2012/057206, (2012).
Todd & Byers, "Volatile Silicone Fluids for Cosmetics," Cosmetics and Toiletries, vol. 91, Jan. 76, pp. 27-32.
Porter, M.R., "Handbook of Surfactants," published by Blackie & Son (Glasgow and London), 1991, pp. 116-178.

* cited by examiner

DYE COMPOSITION USING A PHENOL-DERIVED COUPLER IN A MEDIUM RICH IN FATTY SUBSTANCES, PROCESSES AND DEVICES

CROSS REFERENCE TO RELATED APPLICATIONS

This is a continuation of application Ser. No. 14/114,555, filed Oct. 29, 2013, which is a national stage application of PCT/EP2012/057206, filed internationally on Apr. 19, 2012, which claims priority to U.S. Provisional Application No. 61/483,317, filed on May 6, 2011, as well as French Application No. FR 1153704, filed Apr. 29, 2011, all of which are incorporated herein by reference in their entireties.

One subject of the present invention is a composition for dyeing keratin fibres, comprising one or more fatty substances and one or more surfactants, one or more particular oxidation bases and one or more couplers, of which at least one coupler is chosen from particular phenol derivatives, one or more alkalinizing agents, and the fatty substance content in the composition representing in total at least 25% by weight relative to the total weight of the composition.

The present invention also relates to dyeing processes using this composition in the presence of at least one chemical oxidizing agent, and to a multicompartment device suitable for the use of this composition.

Many people have sought for a long time to modify the colour of their hair and in particular to mask their grey hair.

One of the dyeing methods is "permanent" or oxidation dyeing, which uses dye compositions containing oxidation dye precursors, generally known as oxidation bases. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colouration modifiers, the latter being chosen especially from aromatic meta-diamines, meta-aminophenols, meta-diphenols and certain heterocyclic compounds such as indole compounds. The variety of molecules used as oxidation bases and couplers allows a wide range of colors to be obtained.

It is also possible to use direct dyes in order especially to provide highlights to the colouring obtained. These direct dyes are coloured and colouring molecules that have an affinity for the fibres. Examples that may be mentioned include nitrobenzene, anthraquinone, nitropyridine, azo, xanthene, acridine, azine and triarylmethane direct dyes.

Permanent dyeing processes thus consist in using, with the dye composition, an aqueous composition comprising at least one oxidizing agent, under alkaline pH conditions in the vast majority of cases. The role of this oxidizing agent is to degrade the melanin of the hair, which, depending on the nature of the oxidizing agent present, leads to more or less pronounced lightening of the fibres. The oxidizing agent used is generally hydrogen peroxide.

One of the difficulties encountered during the implementation of the dyeing processes of the prior art arises from the fact that they are carried out under alkaline conditions and that the alkalinizing agents most commonly used are aqueous ammonia and amines. Specifically, the alkalinizing agent makes it possible to adjust the pH of the composition to an alkaline pH to enable activation of the oxidizing agent. In addition, this alkalinizing agent causes swelling of the keratin fibre, with raising of the scales, which promotes the penetration of the oxidizing agent, and also of the dyes, if they are present, essentially oxidation dyes, into the fibre, and thus increases the efficacy of the dyeing or lightening reaction.

However, these alkalinizing agents, and especially aqueous ammonia, cause the user discomfort due to their strong characteristic odour.

Moreover, not only may the user be inconvenienced by the odour, but may also be confronted with greater risks of intolerance, for instance irritation of the scalp, which is especially reflected by stinging.

Furthermore, it is important to obtain colourings that are light fast, but the use of certain couplers, such as meta-phenylenediamines for example, induces degradation by solar radiation.

Moreover, it has been proposed in standard oxidation dyeing to use phenol-derived couplers in the presence of oxidation bases to obtain relatively photostable shades, but, firstly, with couplers of this type, the intensity of the colouring obtained over the whole head of hair (lengths, ends) is relatively poor, and, secondly, the coverage of the roots is not satisfactory.

One of the objectives of the present invention is to propose compositions for dyeing human keratin fibres such as the hair that do not have the drawbacks of existing compositions.

In particular, the composition according to the invention in the presence of a chemical oxidizing agent makes it possible to obtain colours that are satisfactory, especially in terms of coverage or uptake of the colour at the root of the hair, which makes it possible to avoid a "root" effect of the colouring.

It is also possible to obtain colourings that are very stable towards light.

In addition, the invention makes it possible to to achieve substantial degrees of lightening while at the same time colouring, without using persalts or increasing the amount of chemical oxidizing agent or of alkalinizing agent.

These aims and others are achieved by the present invention, one subject of which is thus a composition for dyeing keratin fibres, in particular human keratin fibres such as the hair, comprising:
at least one fatty substance,
at least one surfactant,
at least one oxidation base chosen from heterocyclic oxidation bases,
at least one alkalinizing agent,
at least one coupler of formula (B3), and also salts, optical and geometrical isomers and tautomers, and hydrates:
the fatty substance content representing in total at least 25% by weight relative to the total weight of the composition;
the formula (B3) being the following:

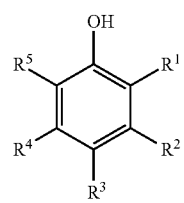

in which:
R$^1$, R$^3$, R$^5$, which may be identical or different, represent:

a hydrogen atom;
an optionally substituted, linear or branched $C_1$-$C_8$ alkyl or $C_3$-$C_8$ alkenyl radical;
a group —SR or —OR in which R represents a hydrogen atom or an optionally substituted, linear or branched $C_1$-$C_8$ alkyl or $C_3$-$C_8$ alkenyl radical;
a ($C_1$-$C_4$)alkylcarbonyl group;
a hydrocarbonyl group (HCO—);
a sulphonic acid group; a carboxylic acid group;
$R^2$, $R^4$, which may be identical or different, represent:
a hydrogen atom;
an optionally substituted, linear or branched $C_1$-$C_8$ alkyl or $C_3$-$C_8$ alkenyl radical;
a group —OR' in which R' represents an optionally substituted, linear or branched $C_1$-$C_8$ alkyl or $C_3$-$C_8$ alkenyl radical;
two groups chosen from $R^1$, $R^2$, $R^3$, $R^4$, $R^5$ and borne by adjacent carbon atoms may form, together with said carbon atoms, a ring or a heterocycle comprising more particularly from 5 to 7 ring members, optionally comprising from one to three heteroatoms, which is optionally substituted, and which is optionally interrupted with one or more carbonyl groups;
at least one of the radicals $R^1$, $R^3$, $R^5$ representing a hydrogen atom and at least one of the radicals $R^2$ or $R^4$ denoting a group —OR' in which R' represents an optionally substituted, linear or branched $C_1$-$C_8$ alkyl or $C_3$-$C_8$ alkenyl radical, it being possible for this radical to form, with the carbon atom bearing it, one of the neighbouring carbon atoms and its substituent, a heterocycle comprising more particularly from 5 to 7 ring members, optionally comprising from one to three heteroatoms, which is optionally substituted, and which is optionally interrupted with one or more carbonyl groups.

Another subject of the invention is a dyeing process using the composition of the invention in the presence of at least one chemical oxidizing agent, and multicompartment devices that enable the use of the composition of the invention.

Thus, the use of the dye composition of the invention in the presence of at least one chemical oxidizing agent leads to powerful, intense, chromatic and/or sparingly selective colourings, i.e. colourings that are uniform along the fibre.

The invention also makes it possible to cover keratin fibres particularly well at their root, especially down to three centimetres from the base of said fibres.

Moreover, the colours obtained after treating the fibres remain stable, in particular towards light.

The invention also makes it possible to reduce the amounts of active agents of the invention such as the dyes and/or alkalinizing agents and/or oxidizing agents without loss of dyeing efficacy of the composition.

Furthermore, the processes according to the invention use formulations that are less malodorous during their application to the hair or during their preparation.

Other features and advantages of the invention will become more clearly apparent on reading the description and the examples that follow.

In the text hereinbelow, unless otherwise indicated, the limits of a range of values are included in that range.

The human keratin fibres treated via the process according to the invention are preferably the hair.

The expression "at least one" is equivalent to the expression "one or more".

Fatty Substances:

As has already been mentioned, the composition of the invention comprises one or more fatty substances.

The term "fatty substance" means an organic compound that is insoluble in water at ordinary temperature (25° C.) and at atmospheric pressure (760 mmHg) (solubility of less than 5%, preferably less than 1% and more preferably still less than 0.1%). They have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (COOH or COO⁻). Particularly, the fatty substances of the invention are neither polyoxyalkylenated nor polyglycerolated.

The term "oil" means a "fatty substance" that is liquid at room temperature (25° C.) and at atmospheric pressure (760 mmHg).

The term "non-silicone oil" means an oil not containing any silicon atoms (Si) and the term "silicone oil" means an oil containing at least one silicon atom.

More particularly, the fatty substances are chosen from $C_6$-$C_{16}$ alkanes, non-silicone oils of animal, plant, mineral or synthetic origin, fatty alcohols, esters of a fatty acid and/or of a fatty alcohol, non-silicone waxes and silicones.

It is recalled that, for the purposes of the invention, fatty alcohols, esters and acids more particularly have at least one linear or branched, saturated or unsaturated hydrocarbon-based group comprising 6 to 30 carbon atoms, which is optionally substituted, in particular with one or more hydroxyl groups (in particular 1 to 4). If they are unsaturated, these compounds may have one to three conjugated or unconjugated carbon-carbon double bonds.

As regards the $C_6$-$C_{16}$ alkanes, they are linear or branched, and possibly cyclic. Examples that may be mentioned include hexane, dodecane and isoparaffins such as isohexadecane and isodecane.

As oils of animal, plant, mineral or synthetic origin that may be used in the composition of the invention, examples that may be mentioned include:
hydrocarbon-based oils of animal origin, such as perhydrosqualene;
triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the names Miglyol® 810, 812 and 818 by the company Dynamit Nobel, jojoba oil and shea butter oil.
linear or branched hydrocarbons of mineral or synthetic origin, containing more than 16 carbon atoms, such as liquid paraffins, petroleum jelly, liquid petroleum jelly, polydecenes, and hydrogenated polyisobutene such as Parleam®;
fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are more particularly chosen from linear or branched, saturated or unsaturated alcohols comprising from 6 to 30 carbon atoms and preferably from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, ° leyl alcohol and linoleyl alcohol.

As regards the esters of a fatty acid and/or of fatty alcohols, which are advantageously different from the triglycerides mentioned above, mention may be made especially of esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The esters of sugar and fatty acids may be chosen especially from the group comprising the esters or mixtures of esters of sugars described previously and of linear or branched, saturated or unsaturated $C_6$-$C_{30}$, and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate®DO by the company Amerchol, which is a methylglucose dioleate.

Examples of esters or mixtures of esters of sugar and of fatty acid that may also be mentioned include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester-triester-polyester;

the sucrose monopalmitostearate-dipalmitostearate sold by the company Goldschmidt under the name Tegosoft® PSE.

The non-silicone wax(es) is (are) chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina); other waxes or waxy raw materials that can be used according to the invention are in particular marine waxes, such as that sold by Sophim under the reference M82, polyethylene waxes or polyolefin waxes in general.

The silicones that can be used in the cosmetic compositions of the present invention are volatile or non-volatile, cyclic, linear or branched silicones, which are unmodified or modified with organic groups, having a viscosity from $5\times10^{-6}$ to $2.5$ m$^2$/s at 25° C., and preferably $1\times10^{-5}$ to $1$ m$^2$/s.

The silicones that can be used in accordance with the invention may be in the form of oils, waxes, resins or gums.

Preferably, the silicone is chosen from polydialkylsiloxanes, especially polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

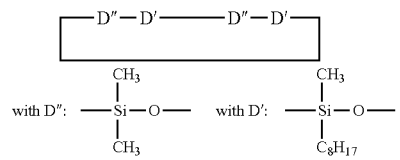

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to ASTM standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that can be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:

the mixtures formed from a hydroxy-terminated polydimethylsiloxane or dimethiconol (CTFA), and from a cyclic polydimethylsiloxane, also known as cyclomethicone (CTFA), such as the product Q2 1401 sold by Dow Corning;

mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and a PDMS oil, such as the product SF 1236 from the company General Electric. The product SF 1236 is the mixture of a gum SE 30 defined above with a viscosity of 20 m$^2$/s and of an oil SF 96 with a viscosity of $5\times10^{-6}$ m$^2$/s. This product preferably comprises 15% of gum SE 30 and 85% of an oil SF 96.

The organopolysiloxane resins that can be used in accordance with the invention are crosslinked siloxane systems containing the following units:

$R_2SiO_{2/2}$, $R_3SiO_{1/2}$, $RSiO_{3/2}$ and $SiO_{4/2}$ in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of resins of the trimethylsiloxysilicate type, sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon-based group.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1\times10^{-5}$ to $5\times10^{-2}$ m$^2$/s at 25° C.

Among these polyalkylarylsiloxanes, examples that may be mentioned include the products sold under the following names:
  the Silbione® oils of the 70 641 series from Rhodia;
  the oils of the Rhodorsil® 70 633 and 763 series from Rhodia;
  the oil Dow Corning 556 Cosmetic Grade Fluid from Dow Corning;
  the silicones of the PK series from Bayer, such as the product PK20;
    the silicones of the PN and PH series from Bayer, such as the products PN1000 and PH1000;
    certain oils of the SF series from General Electric, such as SF 1023, SF 1154, SF 1250 and SF 1265.

Among the organomodified silicones, mention may be made of polyorganosiloxanes comprising:
  polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;
  substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;
  alkoxy groups such as the product sold under the name Silicone Copolymer F-755 by SWS Silicones, and Abil Wax® 2428, 2434 and 2440 by the company Goldschmidt.

Preferably, the fatty substances do not comprise any $C_2$-$C_3$ oxyalkylene units or any glycerolated units.

More particularly, the fatty substances are chosen from compounds that are liquid or pasty at room temperature (25° C.) and at atmospheric pressure.

Preferably, the fatty substance is a compound that is liquid at a temperature of 25° C. and at atmospheric pressure.

The fatty substances are advantageously chosen from $C_6$-$C_{16}$ alkanes, non-silicone oils of plant, mineral or synthetic origin, fatty alcohols, esters of a fatty acid and/or of a fatty alcohol, and silicones, or mixtures thereof.

Preferably, the fatty substance is chosen from liquid petroleum jelly, $C_6$-$C_{16}$ alkanes, polydecenes, liquid esters of a fatty acid and/or of a fatty alcohol, and liquid fatty alcohols, or mixtures thereof.

Better still, the fatty substance is chosen from liquid petroleum jelly, $C_6$-$C_{16}$ alkanes and polydecenes.

The composition according to the invention comprises at least 25% by weight of fatty substances.

The composition according to the invention more particularly has a fatty substance content ranging from 25% to 80% by weight, preferably from 30% to 70% by weight and more advantageously still from 30% to 60% by weight relative to the weight of the composition.

Surfactants:

The composition of the invention also comprises one or more surfactants.

In particular, the surfactant(s) is (are) chosen from anionic, amphoteric, zwitterionic, cationic and nonionic surfactants, and preferentially nonionic surfactants.

The term "anionic surfactant" means a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH, =PO$^-$, the anionic parts comprising a cationic counterion such as an alkali metal, an alkaline-earth metal or an ammonium.

Mention may be made, as examples of anionic surfactants that can be used in the composition according to the invention, of alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphoacetates, acyl sarcosinates, acyl glutamates, alkyl sulphosuccinamates, acyl isethionates and N-acyl taurates, salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulphosuccinates.

When the anionic surfactant(s) is (are) in salt form, it (they) may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, and in particular sodium or magnesium salts.

Among the anionic surfactants mentioned, use is preferably made of ($C_6$-$C_{24}$)alkyl sulphates, ($C_6$-$C_{24}$)alkyl ether sulphates comprising from 2 to 50 ethylene oxide units, especially in the form of alkali metal, ammonium, amino alcohol and alkaline-earth metal salts, or a mixture of these compounds.

In particular, it is preferred to use ($C_{12}$-$C_{20}$)alkyl sulphates, ($C_{12}$-$C_{20}$)alkyl ether sulphates comprising from 2 to 20 ethylene oxide units, especially in the form of alkali metal, ammonium, amino alcohol and alkaline-earth metal salts, or a mixture of these compounds. Better still, it is preferred to use sodium lauryl ether sulphate containing 2.2 mol of ethylene oxide.

The amphoteric or zwitterionic surfactant(s), which is (are) preferably non-silicone surfactant(s), which can be used in the present invention may especially be derivatives of optionally quaternized secondary or tertiary aliphatic amines, in which derivatives the aliphatic group is a linear or branched chain comprising from 8 to 22 carbon atoms, said amine derivatives containing at least one anionic group, for instance a carboxylate, sulphonate, sulphate, phosphate or phosphonate group. Mention may be made in particular of ($C_8$-$C_{20}$)alkylbetaines, sulphobetaines, ($C_8$-$C_{20}$)alkylamido($C_3$-$C_8$)alkylbetaines and ($C_3$-$C_{20}$)alkylamido($C_6$-$C_8$)alkylsulphobetaines.

Among the optionally quaternized secondary or tertiary aliphatic amine derivatives that can be used, as defined above, mention may also be made of the compounds of respective structures (A1) and (A2) below:

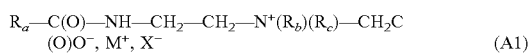
$$R_a\text{—C(O)—NH—CH}_2\text{—CH}_2\text{—N}^+(R_b)(R_c)\text{—CH}_2\text{C(O)O}^-, M^+, X^- \quad (A1)$$

in which formula (A1):
- $R_a$ represents a $C_{10}$-$C_{30}$ alkyl or alkenyl group derived from an acid $R_a$—COOH preferably present in hydrolyzed coconut oil, or a heptyl, nonyl or undecyl group;
- $R_b$ represents a β-hydroxyethyl group; and
- $R_c$ represents a carboxymethyl group;
- $M^+$ represents a cationic counterion derived from an alkali metal or alkaline-earth metal, such as sodium, an ammonium ion or an ion derived from an organic amine, and
- $X^-$ represents an organic or inorganic anionic counterion, such as that chosen from halides, acetates, phosphates, nitrates, ($C_1$-$C_4$)alkyl sulphates, ($C_1$-$C_4$) alkyl or ($C_1$-$C_4$)alkylaryl sulphonates, in particular methyl sulphate and ethyl sulphate; or alternatively $M^+$ and $X^-$ are absent;

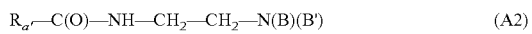
$$R_{a'}\text{—C(O)—NH—CH}_2\text{—CH}_2\text{—N(B)(B')} \quad (A2)$$

in which formula (A2):
- B represents the group —$CH_2$—$CH_2$—O—X';
- B' represents the group —$(CH_2)_z$Y', with z=1 or 2;
- X' represents the group —$CH_2$—C(O)OH, —$CH_2$—C(O)OZ', —$CH_2$—$CH_2$—C(O)OH, —$CH_2$—$CH_2$—C(O)OZ', or a hydrogen atom;
- Y' represents the group —C(O)OH, —C(O)OZ', —$CH_2$—CH(OH)—$SO_3$H or the group —$CH_2$—CH(OH)—$SO_3$—Z';
- Z' represents a cationic counterion derived from an alkali metal or alkaline-earth metal, such as sodium, an ammonium ion or an ion derived from an organic amine;
- $R_{a'}$ represents a $C_{10}$-$C_{30}$ alkyl or alkenyl group of an acid $R_a$—C(O)OH preferably present in coconut oil or in hydrolyzed linseed oil, an alkyl group, especially a $C_{17}$ alkyl group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylloamphodiacetate, disodium cocoamphodipropionate, disodium lauroamphodipropionate, disodium caprylamphodipropionate, disodium caprylloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above, use is preferably made of ($C_8$-$C_{20}$)alkylbetaines such as cocobetaine, and ($C_8$-$C_{20}$)alkylamido($C_3$-$C_8$)alkylbetaines such as cocamidopropylbetaine, and mixtures thereof. More preferentially, the amphoteric or zwitterionic surfactant(s) is (are) chosen from cocamidopropylbetaine and cocobetaine.

The cationic surfactant(s) that can be used in the composition according to the invention comprise, for example, salts of optionally polyoxyalkylenated primary, secondary or tertiary fatty amines, quaternary ammonium salts, and mixtures thereof.

Examples of quaternary ammonium salts that may especially be mentioned include:
those corresponding to the general formula (A4) below:

$$\begin{bmatrix} R_8 & R_{10} \\ & N & \\ R_9 & R_{11} \end{bmatrix}^+ X^- \quad (A4)$$

in which formula (A4):
- $R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and
- $X^-$ represents an organic or inorganic anionic counterion, such as that chosen from halides, acetates, phosphates, nitrates, ($C_1$-$C_4$)alkyl sulphates, ($C_1$-$C_4$)alkyl or ($C_1$-$C_4$)alkylaryl sulphonates, in particular methyl sulphate and ethyl sulphate.

The aliphatic groups of $R_8$ to $R_{11}$ may also comprise heteroatoms especially such as oxygen, nitrogen, sulphur and halogens.

The aliphatic groups of $R_8$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl, $X^-$ is an anionic counterion chosen from halides, phosphates, acetates, lactates, ($C_1$-$C_4$)alkyl sulphates, ($C_1$-$C_4$)alkyl or ($C_1$-$C_4$)alkylaryl sulphonates.

Among the quaternary ammonium salts of formula (A4), preference is given firstly to tetraalkylammonium chlorides, for instance dialkyldimethylammonium or alkyltrimethylammonium chlorides in which the alkyl group contains approximately from to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulphate, dipalmitoylethylhydroxyethylammonium methosulphate or distearoylethylhydroxyethylammonium methosulphate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (A5) below:

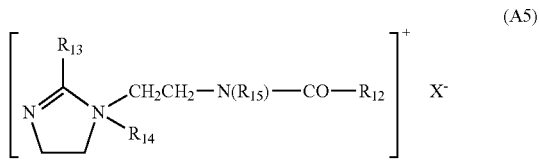

(A5)

in which formula (A5):
R$_{12}$ represents an alkenyl or alkyl group comprising from 8 to 30 carbon atoms, for example tallow fatty acid derivatives;
R$_{13}$ represents a hydrogen atom, a C$_1$-C$_4$ alkyl group or an alkenyl or alkyl group comprising from 8 to 30 carbon atoms;
R$_{14}$ represents a C$_1$-C$_4$ alkyl group;
R$_{15}$ represents a hydrogen atom or a C$_1$-C$_4$ alkyl group;
X$^-$ represents an organic or inorganic anionic counterion, such as that chosen from halides, phosphates, acetates, lactates, (C$_1$-C$_4$)alkyl sulphates, (C$_1$-C$_4$)alkyl or (C$_1$-C$_4$)alkylaryl sulphonates.

R$_{12}$ and R$_{13}$ preferably denote a mixture of alkenyl or alkyl groups comprising from 12 to 21 carbon atoms, for example tallow fatty acid derivatives, R$_{14}$ denotes a methyl group, and R$_{15}$ denotes a hydrogen atom. Such a product is sold, for example, under the name Rewoquat® W 75 by the company Rewo;

quaternary diammonium or triammonium salts, particularly of formula (A6) below:

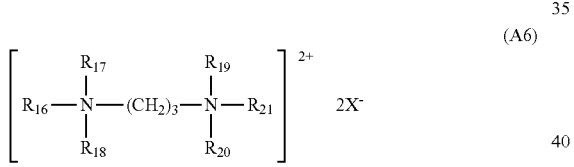

(A6)

in which formula (III):
R$_{16}$ denotes an alkyl group comprising approximately from 16 to 30 carbon atoms, which is optionally hydroxylated and/or interrupted with one or more oxygen atoms;
R$_{17}$ is chosen from hydrogen, an alkyl group comprising from 1 to 4 carbon atoms or a group —(CH$_2$)$_3$—N$^+$(R$_{16a}$)(R$_{17a}$)(R$_{18a}$), X$^-$;
R$_{16a}$, R$_{17a}$, R$_{18a}$, R$_{18}$, R$_{19}$, R$_{20}$ and R$_{21}$, which may be identical or different, are chosen from hydrogen and an alkyl group comprising from 1 to 4 carbon atoms; and
X$^-$, which may be identical or different, represents an organic or inorganic anionic counterion, such as that chosen from halides, acetates, phosphates, nitrates, (C$_1$-C$_4$)alkyl sulphates, (C$_1$-C$_4$)alkyl or (C$_1$-C$_4$)alkylaryl sulphonates, in particular methyl sulphate and ethyl sulphate.

Such compounds are, for example, Finquat CT-P, sold by the company Finetex (Quaternium 89), and Finquat CT, sold by the company Finetex (Quaternium 75);

quaternary ammonium salts containing one or more ester functions, such as those of formula (A7) below:

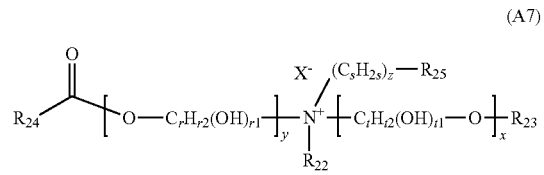

(A7)

in which formula (A7):
R$_{22}$ is chosen from C$_1$-C$_6$ alkyl and C$_1$-C$_6$ hydroxyalkyl or dihydroxyalkyl groups,
R$_{23}$ is chosen from:
the group

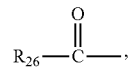

linear or branched, saturated or unsaturated C$_1$-C$_{22}$ hydrocarbon-based groups R$_{27}$,
a hydrogen atom,
R$_{25}$ is chosen from:
the group

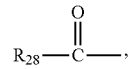

linear or branched, saturated or unsaturated C$_1$-C$_6$ hydrocarbon-based groups R$_{29}$,
a hydrogen atom,
R$_{24}$, R$_{26}$ and R$_{28}$, which may be identical or different, are chosen from linear or branched, saturated or unsaturated C$_7$-C$_{21}$ hydrocarbon-based groups;
r, s and t, which may be identical or different, are integers ranging from 2 to 6,
r1 and t1, which may be identical or different, are equal to 0 or 1, with r2+r1=2r and t1+t2=2t,
y is an integer ranging from 1 to 10,
x and z, which may be identical or different, are integers ranging from 0 to 10,
X$^-$ represents an organic or inorganic anionic counterion,
with the proviso that the sum x+y+z is from 1 to 15, that when x is 0 then R$_{23}$ denotes R$_{27}$, and that when z is 0 then R$_{25}$ denotes R$_{29}$.

The alkyl groups R$_{22}$ may be linear or branched, and more particularly linear.

Preferably, R$_{22}$ denotes a methyl, ethyl, hydroxyethyl or dihydroxypropyl group, and more particularly a methyl or ethyl group.

Advantageously, the sum x+y+z is from 1 to 10.

When R$_{23}$ is a hydrocarbon-based group R$_{27}$, it may be long and contain from 12 to 22 carbon atoms, or may be short and contain from 1 to 3 carbon atoms.

When R$_{25}$ is a hydrocarbon-based group R$_{29}$, it preferably contains 1 to 3 carbon atoms.

Advantageously, R$_{24}$, R$_{26}$ and R$_{28}$, which may be identical or different, are chosen from linear or branched, saturated or unsaturated C$_{11}$-C$_{21}$ hydrocarbon-based groups, and more particularly from linear or branched, saturated or unsaturated C$_{11}$-C$_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion $X^-$ is preferably a halide, such as chloride, bromide or iodide; a $(C_1-C_4)$alkyl sulphate or a $(C_1-C_4)$alkyl or $(C_1-C_4)$alkylaryl sulphonate. However, it is possible to use methanesulphonate, phosphate, nitrate, tosylate, an anion derived from an organic acid, such as acetate or lactate, or any other anion that is compatible with the ammonium containing an ester function.

The anionic counterion $X^-$ is even more particularly chloride, methyl sulphate or ethyl sulphate.

Use is made more particularly, in the composition according to the invention, of the ammonium salts of formula (A7) in which:

$R_{22}$ denotes a methyl or ethyl group,
x and y are equal to 1,
z is equal to 0 or 1,
r, s and t are equal to 2,
$R_{23}$ is chosen from:
the group

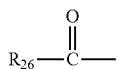

methyl, ethyl or $C_{14}-C_{22}$ hydrocarbon-based groups,
a hydrogen atom,
$R_{25}$ is chosen from:
the group

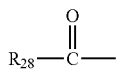

a hydrogen atom,
$R_{24}$, $R_{26}$ and $R_{28}$, which may be identical or different, are chosen from linear or branched, saturated or unsaturated $C_{13}-C_{17}$ hydrocarbon-based groups, and preferably from linear or branched, saturated or unsaturated $C_{13}-C_{17}$ alkyl and alkenyl groups.

Advantageously, the hydrocarbon-based radicals are linear.

Among the compounds of formula (A7), examples that may be mentioned include salts, especially the chloride or methyl sulphate, of diacyloxyethyldimethylammonium, diacyloxyethylhydroxyethylmethylammonium, monoacyloxyethyldihydroxyethyl-methylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulphate, preferably dimethyl or diethyl sulphate, methyl methanesulphonate, methyl para-toluenesulphonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of monoesters, diesters and triesters with a weight majority of diester salts.

It is also possible to use the ammonium salts containing at least one ester function that are described in U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulphate, and mixtures thereof.

Examples of nonionic surfactants that can be used in the composition used according to the invention are described, for example, in the "Handbook of Surfactants" by M. R. Porter, published by Blackie & Son (Glasgow and London), 1991, pp. 116-178. They are especially chosen from alcohols, α-diols and $(C_1-C_{20})$alkylphenols, these compounds being polyethoxylated, polypropoxylated or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkyl glucamine and of N-acyl methylglucamine, aldobionamides and amine oxides.

The nonionic surfactants are more particularly chosen from monooxyalkylenated or polyoxyalkylenated, monoglycerolated or polyglycerolated nonionic surfactants. The oxyalkylenated units are more particularly oxyethylenated or oxypropylenated units, or a combination thereof, preferably oxyethylenated units.

Examples of oxyalkylenated nonionic surfactants that may be mentioned include:
oxyalkylenated $(C_8-C_{24})$alkylphenols;
saturated or unsaturated, linear or branched, oxyalkylenated $C_8-C_{30}$ alcohols;
saturated or unsaturated, linear or branched, oxyalkylenated $C_8-C_{30}$ amides;
esters of saturated or unsaturated, linear or branched $C_8-C_{30}$ acids and of polyethylene glycols;
polyoxyethylenated esters of saturated or unsaturated, linear or branched $C_8-C_{30}$ acids and of sorbitol;
saturated or unsaturated oxyethylenated plant oils;

condensates of ethylene oxide and/or of propylene oxide, inter alia, alone or as mixtures;

oxyethylenated and/or oxypropylenated silicones.

The surfactants contain a number of moles of ethylene oxide and/or of propylene oxide of between 1 and 100, preferably between 2 and 50 and preferably between 2 and 30. Advantageously, the nonionic surfactants do not comprise any oxypropylenated units.

In accordance with one preferred embodiment of the invention, the oxyalkylenated nonionic surfactants are chosen from oxyethylenated $C_8$-$C_{30}$ alcohols comprising from 1 to 100 mol of ethylene oxide; polyoxyethylenated esters of linear or branched, saturated or unsaturated $C_8$-$C_{30}$ acids and of sorbitol comprising from 1 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the formula (A8) below:

$$R_{29}O-[CH_2-CH(CH_2OH)-O]_m-H \quad (A8)$$

in which formula (A8):

$R_{29}$ represents a linear or branched $C_8$-$C_{40}$ and preferably $C_8$-$C_{30}$ alkyl or alkenyl radical; and m represents a number ranging from 1 to 30 and preferably from 1 to 10.

As examples of compounds of formula (A8) that are suitable within the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Preferably, the surfactant used in the process of the invention in the composition is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated.

Preferably, the surfactant(s) is (are) chosen from nonionic surfactants or from anionic surfactants. More particularly, the surfactant(s) present in the composition is (are) chosen from nonionic surfactants.

More preferably still, the nonionic surfactants are chosen from polyoxyethylenated sorbitol esters and polyoxyethylenated fatty alcohols, and mixtures thereof.

In the composition of the invention, the amount of surfactant(s) in the composition preferably ranges from 0.1% to 50% by weight and better still from 0.5% to 20% by weight relative to the total weight of the composition.

Oxidation Bases:

The composition of the invention comprises one or more oxidation bases chosen from heterocyclic bases, and salts thereof.

The heterocyclic bases are more particularly chosen from pyridine derivatives, pyrimidine derivatives and pyrazole derivatives, and the addition salts thereof.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the in the dyeing process according to the invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in the patents DE 2359399; JP 88-169571; JP 05-63124; EP 0 770 375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)

amino-1-methylpyrazole, and the addition salts thereof. Use may also be made of 4,5-diamino-1-(β-methoxyethyl)pyrazole.

Use will preferably be made of a 4,5-diaminopyrazole and more preferably still of 4,5-diamino-1-(β-hydroxyethyl) pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-Diamino-6,7-dihydro-1H,5H-pyrazolo[1,2-a]pyrazol-1-one and/or a salt thereof.

As heterocyclic bases, use will preferably be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

The oxidation base(s) present in the composition advantageously each represent(s) from 0.0001% to 10% by weight relative to the total weight of the composition, and preferably from 0.005% to 5% by weight relative to the total weight of the composition.

Additional Oxidation Base:

The composition of the invention may optionally comprise one or more additional oxidation bases, other than the aforementioned heterocyclic bases and in particular chosen from benzene oxidation bases and salts thereof.

The benzene oxidation bases are in fact chosen from para-phenylenediamines, bis(phenyl)alkylenediamines, para-aminophenols, ortho-aminophenols, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

The additional oxidation base(s), if the composition comprises the latter, each advantageously represent from 0.0001% to 10% by weight relative to the total weight of the composition and preferably from 0.005% to 5% by weight relative to the total weight of the composition.

Phenol-Derived Couplers of Formula (B3):

The composition according to the invention comprises one or more couplers of formula (B3) and also salts thereof, optical and geometrical isomers and tautomers thereof, and hydrates thereof:

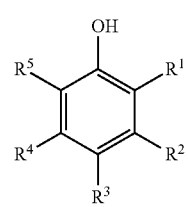

in which formula:
R$^1$, R$^3$, R$^5$, which may be identical or different, represent:
  a hydrogen atom;
  an optionally substituted, linear or branched $C_1$-$C_8$ alkyl or $C_3$-$C_8$ alkenyl radical;

a group —SR or —OR in which R represents a hydrogen atom or an optionally substituted, linear or branched $C_1$-$C_8$ alkyl or $C_3$-$C_8$ alkenyl radical;
a ($C_1$-$C_4$)alkylcarbonyl group;
a hydrocarbonyl group (HCO—);
a sulphonic acid group; a carboxylic acid group;
$R^2$, $R^4$, which may be identical or different, represent:
a hydrogen atom;
an optionally substituted, linear or branched $C_1$-$C_8$ alkyl or $C_3$-$C_8$ alkenyl radical;
a group —OR' in which R' represents an optionally substituted, linear or branched $C_1$-$C_8$ alkyl or $C_3$-$C_8$ alkenyl radical;
two groups chosen from $R^1$, $R^2$, $R^3$, $R^4$, $R^5$ and borne by adjacent carbon atoms may form, together with said carbon atoms, a ring or, preferably, a heterocycle comprising more particularly from 5 to 7 ring members, optionally comprising from one to three heteroatoms, which is optionally substituted, and which is optionally interrupted with one or more carbonyl groups;
at least one of the radicals $R^1$, $R^3$, $R^5$ representing a hydrogen atom and at least one of the radicals $R^2$ or $R^4$ denoting a group —OR' in which R' represents an optionally substituted, linear or branched $C_1$-$C_8$ alkyl or $C_3$-$C_8$ alkenyl radical, it being possible for this radical to form, with the carbon atom bearing it, one of the neighbouring carbon atoms and its substituent, a heterocycle comprising more particularly from 5 to 7 ring members, optionally comprising from one to three heteroatoms, which is optionally substituted, and which is optionally interrupted with one or more carbonyl groups.

According to the invention, and unless otherwise specified, a linear or branched alkyl or alkenyl radical is said to be substituted when it bears one or more groups chosen from the following groups:
hydroxyl,
$C_1$-$C_4$ alkoxy,
amino,
mono($C_1$-$C_4$)alkylamino or di($C_1$-$C_4$)alkylamino, optionally substituted with one or more hydroxyl or amino groups,
tri(C1-C4)alkylammonium,
carboxyl.

When the group is cyclic or heterocyclic, the latter may be substituted on a carbon atom with one or more groups such as those mentioned for alkyl or alkenyl groups, and also with one or more $C_1$-$C_4$ alkyl radicals.

If the heteroatom(s) of the heterocycle is (are) substituted, it (they) is (are) substituted with a $C_1$-$C_4$ alkyl radical.

Furthermore, said ring or heterocycle does not advantageously comprise a carbon-carbon double bond other than that of the benzene ring to which it is fused.

According to one particular variant of the invention, the coupler(s) of formula (B3) is (are) chosen from those in which:
$R^1$, $R^3$, $R^5$, which may be identical or different, represent:
a hydrogen atom;
a linear or branched $C_1$-$C_8$ alkyl or $C_3$-$C_8$ alkenyl radical, optionally substituted with one or more hydroxyl, amino or carboxyl groups;
a group —OR in which R represents a hydrogen atom or a linear or branched $C_1$-$C_4$ alkyl radical;
a ($C_1$-$C_4$)alkylcarbonyl group;
a carboxylic acid group;

$R^2$, $R^4$, which may be identical or different, represent:
a hydrogen atom;
a linear or branched $C_1$-$C_4$ alkyl radical;
a group —OR' in which R' represents a linear or branched $C_1$-$C_8$, preferably $C_1$-$C_4$ alkyl radical;
two groups chosen from $R^1$, $R^2$, $R^3$, $R^4$, $R^5$ and borne by adjacent carbon atoms may form, together with said carbon atoms, a heterocycle comprising 5 or 6 ring members, comprising one or two identical or different heteroatoms chosen from an oxygen atom or a sulphur atom, which is optionally interrupted with at least one carbonyl group and which is optionally substituted with one or more $C_1$-$C_4$ alkyl radicals;
at least one of the radicals $R^1$, $R^3$, $R^5$ representing a hydrogen atom and at least one of the radicals $R^2$ or $R^4$ denoting a group —OR' in which R' represents an optionally substituted, linear or branched $C_1$-$C_8$ alkyl or $C_3$-$C_8$ alkenyl radical, it being possible for this radical to form, with the carbon atom bearing it, one of the neighbouring carbon atoms and its substituent, a heterocycle comprising more particularly from 5 to 7 ring members, optionally comprising from one to three heteroatoms, which is optionally substituted, and which is optionally interrupted with one or more carbonyl groups.

In accordance with a preferred embodiment of the invention, the coupler(s) of formula (B3) is (are) chosen from those in which:
$R^1$, $R^3$, $R^5$, which may be identical or different, represent:
a hydrogen atom;
a linear or branched $C_1$-$C_6$ alkyl radical;
a group —OR in which R represents a hydrogen atom or a linear or branched $C_1$-$C_4$ alkyl radical;
a ($C_1$-$C_4$)alkylcarbonyl group;
a carboxylic acid group;
$R^2$, $R^4$, which may be identical or different, represent:
a hydrogen atom;
a linear or branched $C_1$-$C_4$ alkyl radical;
a group —OR' in which R' represents a hydrogen atom or a linear or branched $C_1$-$C_8$, preferably $C_1$-$C_4$ alkyl radical;
two groups chosen, on the one hand, from $R^1$ and $R^2$ and, on the other hand, from $R^4$ and $R^5$ may form, together with the carbon atoms to which they are attached, a heterocycle comprising 5 or 6 ring members, comprising one or two oxygen atoms, which is optionally interrupted with at least one carbonyl group and which is optionally substituted with one or more $C_1$-$C_4$ alkyl radicals;
at least one of the radicals $R^1$, $R^3$, $R^5$ representing a hydrogen atom and at least one of the radicals $R^2$ or $R^4$ denoting a group —OR' in which R' represents an optionally substituted, linear or branched $C_1$-$C_8$ alkyl or $C_3$-$C_8$ alkenyl radical, it being possible for this radical to form, with the carbon atom bearing it, one of the neighbouring carbon atoms and its substituent, a heterocycle comprising more particularly from 5 to 7 ring members, optionally comprising from one to three heteroatoms, which is optionally substituted, and which is optionally interrupted with one or more carbonyl groups.

Preferably, the coupler(s) of formula (B3) is (are) chosen from the following compounds, and salts thereof, optical and geometrical isomers and tautomers thereof, and hydrates thereof:

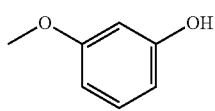

3-methoxyphenol

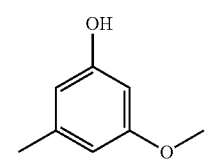

3-methoxy-5-methylphenol

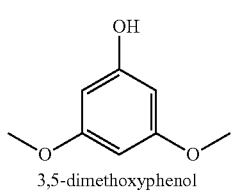

3,5-dimethoxyphenol

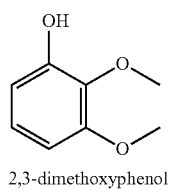

2,3-dimethoxyphenol

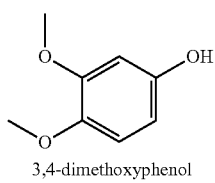

3,4-dimethoxyphenol

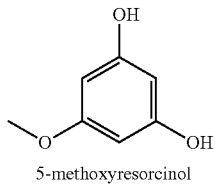

5-methoxyresorcinol

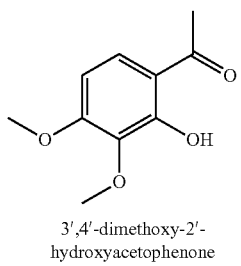

3′,4′-dimethoxy-2′-hydroxyacetophenone

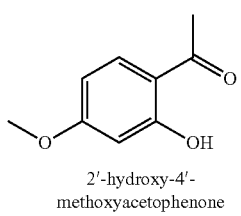

2′-hydroxy-4′-methoxyacetophenone 150-19-6

3209-13-0

500-99-2

5150-42-5

2033-89-8

2174-64-3

5396-18-9

552-41-0

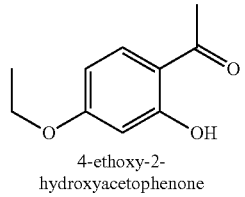

4-ethoxy-2-hydroxyacetophenone

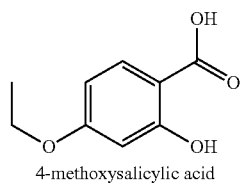

4-methoxysalicylic acid

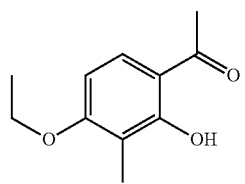

4′-ethoxy-2′-hydroxy-3′-ethylacetophenone

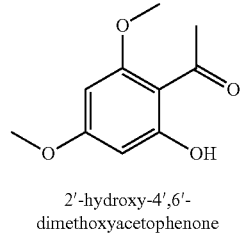

2′-hydroxy-4′,6′-dimethoxyacetophenone

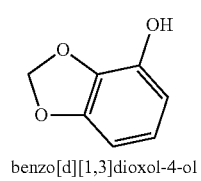

benzo[d][1,3]dioxol-4-ol

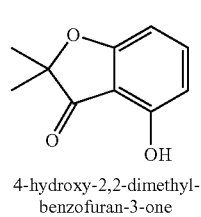

4-hydroxy-2,2-dimethyl-benzofuran-3-one

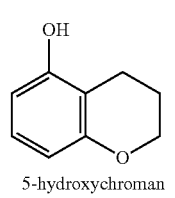

5-hydroxychroman 37470-42-1

2237-36-7

536723-94-1

90-24-4

69393-72-2

81407-92-3

942-56-3

-continued

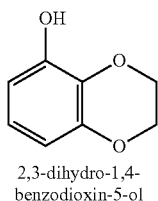

2,3-dihydro-1,4-
benzodioxin-5-ol 10288-36-5

Preferably, the coupler(s) of formula (B3) is (are) chosen from the following compounds, and salts thereof, optical and geometrical isomers and tautomers thereof, and hydrates thereof:

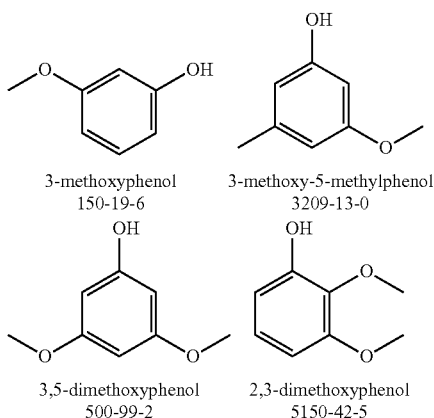

3-methoxyphenol
150-19-6

3-methoxy-5-methylphenol
3209-13-0

3,5-dimethoxyphenol
500-99-2

2,3-dimethoxyphenol
5150-42-5

The coupler(s) of formula (B3) each advantageously represent(s) from 0.0001% to 10% by weight relative to the total weight of the composition and preferably from 0.005% to 5% by weight relative to the total weight of the composition of the invention.

Additional Couplers:

The composition of the invention may optionally comprise one or more additional couplers other than the couplers of formula (B3).

Among these additional couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

The additional coupler(s), if it (they) is (are) present, each advantageously represent from 0.0001% to 10% by weight relative to the total weight of the composition, and preferably from 0.005% to 5% by weight relative to the total weight of the composition.

In general, the addition salts of the oxidation bases and couplers that can be used within the context of the invention are especially chosen from the addition salts with an acid such as the hydrochlorides, hydrobromides, sulphates, citrates, succinates, tartrates, lactates, tosylates, benzenesulphonates, phosphates and acetates.

Additional Dyes:

The composition of the invention may also comprise one or more direct dyes.

The latter dyes are more particularly chosen from ionic or nonionic species, preferably cationic or nonionic species. These direct dyes may be synthetic or of natural origin.

Examples of suitable direct dyes that may be mentioned include azo direct dyes; methine direct dyes; carbonyl direct dyes; azine direct dyes; nitro (hetero)aryl direct dyes; tri (hetero)arylmethane direct dyes; porphyrin direct dyes; phthalocyanine direct dyes, and natural direct dyes, alone or as mixtures.

More particularly, the azo dyes comprise an —N=N— function in which the two nitrogen atoms are not simultaneously engaged in a ring. However, it is not excluded for one of the two nitrogen atoms of the sequence —N=N— to be engaged in a ring.

The dyes of the methine family are more particularly compounds comprising at least one sequence chosen from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of the type such as methines, azomethines, monoarylmethanes and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures.

Among the natural direct dyes that can be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent(s) from 0.0001% to 10% by weight and preferably from 0.005% to 5% by weight of the total weight of the composition.

The Alkalinizing Agents:

The composition according to the invention also comprises one or more alkalinizing agents.

The alkalinizing agent(s) may be mineral or organic or hybrid.

The mineral alkalinizing agent(s) is (are) preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkalinizing agent(s) is (are) preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chains comprising more than ten carbon atoms.

The organic alkalinizing agent(s) is (are) chosen, for example, from alkanolamines, oxyethylenated and/or oxypropylenated ethylenediamines, amino acids and the compounds of formula (I) below:

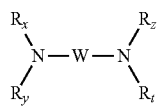

in which formula (I) W is a $C_1$-$C_6$ divalent alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl or $C_1$-$C_6$ hydroxyalkyl or $C_1$-$C_6$ aminoalkyl radical.

Examples of amines of formula (I) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that can be used are of natural or synthetic origin, in their L, D or racemic form, and comprise at least one acid function chosen more particularly from carboxylic acid, sulphonic acid, phosphonic acid or phosphoric acid functions. The amino acids may be in neutral or ionic form.

As amino acids that can be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (II) below, and also the salts thereof:

in which formula (II) R represents a group chosen from:

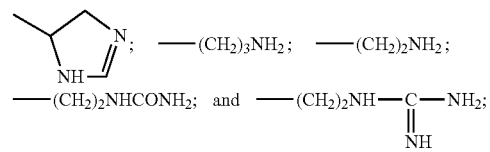

The compounds corresponding to formula (II) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that can be used in the present invention, mention may be made especially of carnosine, anserine and balenine.

The organic amine may also be chosen from compounds comprising a guanidine function. As amines of this type that can be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulphonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkalinizing agent(s) present in the composition of the invention is (are) chosen from alkanolamines, amino acids in neutral or ionic form, in particular basic amino acids, and preferably corresponding to those of formula (II). More preferably still, the alkalinizing agent(s) is (are) chosen from monoethanolamine (MEA) and basic amino acids in neutral or ionic form.

Advantageously, the composition according to the invention has a content of alkalinizing agent(s) ranging from 0.01% to 30% by weight and preferably from 0.1% to 20% by weight relative to the weight of the composition.

According to a first particular embodiment, the composition according to the invention or else the process according to the invention does not use aqueous ammonia, or a salt thereof, as alkalinizing agent.

According to a second embodiment, if the composition or if the process according to the invention does use aqueous ammonia, or a salt thereof, as alkalinizing agent, its content should advantageously not exceed 0.03% by weight (expressed as $NH_3$), preferably should not exceed 0.01% by weight, relative to the weight of the composition of the invention.

Preferably, if the composition comprises aqueous ammonia, or a salt thereof, then the amount of alkalinizing agent(s) other than the aqueous ammonia is greater than that of the aqueous ammonia (expressed as $NH_3$).

Chemical Oxidizing Agent:

The composition of the invention may also comprise one or more chemical oxidizing agents.

The composition of the invention preferably comprises one or more chemical oxidizing agents.

The expression "chemical oxidizing agent" means an oxidizing agent other than atmospheric oxygen.

More particularly, the chemical oxidizing agent(s) is (are) chosen from hydrogen peroxide, urea peroxide, alkali metal bromates, peroxygenated salts, for instance persulphates, perborates, peracids and precursors thereof and percarbonates of alkali metals or alkaline-earth metals.

This oxidizing agent is advantageously formed from hydrogen peroxide especially in aqueous solution (aqueous hydrogen peroxide solution), the concentration of which may range more particularly from 0.1% to 50% by weight, more preferably still from 0.5% to 20% by weight and better still from 1% to 15% by weight relative to the weight of the composition.

Preferably, the composition of the invention does not contain any peroxygenated salts.

Solvent:

The composition according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The solvent(s), if it is (they are) present, represent(s) a content usually ranging from 1% to 40% by weight and preferably from 5% to 30% by weight relative to the weight of the composition.

Other Additives:

The composition according to the invention may also contain various adjuvants conventionally used in hair dye compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of composition.

The composition may especially comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulphates, alkylaryl sulphonates and amine oxides, and mixtures thereof.

Organophilic clays that may be mentioned include quaternium-18 bentonites such as those sold under the names Bentone 3, Bentone 38 and Bentone 38V by the company Rheox, Tixogel VP by the company United Catalyst, Claytone 34, Claytone 40 and Claytone XL by the company Southern Clay; stearalkonium bentonites such as those sold under the names Bentone 27 by the company Rheox, Tixogel LG by the company United Catalyst and Claytone AF and Claytone APA by the company Southern Clay; and quaternium-18/benzalkonium bentonites such as those sold under the names Claytone HT and Claytone PS by the company Southern Clay.

The fumed silicas may be obtained by high-temperature hydrolysis of a volatile silicon compound in an oxyhydrogen flame, producing a finely divided silica. This process makes it possible especially to obtain hydrophilic silicas having a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica via chemical reaction in order to reduce the number of silanol groups. It is especially possible to substitute silanol groups with hydrophobic groups: a hydrophobic silica is then obtained.

The hydrophobic groups may be:
trimethylsiloxyl groups, which are obtained especially by treating fumed silica in the presence of hexamethyldisilazane. Silicas thus treated are known as "silica silylate" according to the CTFA (6th Edition, 1995). They are sold, for example, under the references Aerosil R812® by the company Degussa and Cab-O-Sil TS-530® by the company Cabot.
dimethylsilyloxyl or polydimethylsiloxane groups, which are especially obtained by treating fumed silica in the presence of polydimethylsiloxane or dimethyldichlorosilane. Silicas thus treated are known as "silica dimethyl silylate" according to the CTFA (6th Edition, 1995). They are sold, for example, under the references Aerosil R972® and Aerosil R974® by the company Degussa, and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the mineral thickener represents from 1% to 30% by weight relative to the weight of the composition.

The composition may also comprise one or more organic thickeners.

These thickeners may be chosen from fatty acid amides (coconut monoethanolamide or diethanolamide, oxyethylenated alkyl ether carboxylic acid monoethanolamide), polymeric thickeners such as cellulose-based thickeners (hydroxyethyl cellulose, hydroxypropyl cellulose or carboxymethyl cellulose), guar gum and derivatives thereof (hydroxypropyl guar), gums of microbial origin (xanthan gum, scleroglucan gum), crosslinked homopolymers of acrylic acid or of acrylamidopropanesulphonic acid and associative polymers (polymers comprising hydrophilic regions and hydrophobic regions having a fatty chain (alkyl or alkenyl chain comprising at least 10 carbon atoms) that are capable, in an aqueous medium, of reversibly associating with one another or with other molecules).

According to one particular embodiment, the organic thickener is chosen from cellulose-based thickeners (hydroxyethyl cellulose, hydroxypropyl cellulose or carboxymethyl cellulose), guar gum and derivatives thereof (hydroxypropyl guar), gums of microbial origin (xanthan gum, scleroglucan gum) and crosslinked homopolymers of acrylic acid or of acrylamidopropanesulphonic acid, and preferably from cellulose-based thickeners in particular with hydroxyethyl cellulose.

The content of organic thickener(s), if it is (they are) present, usually ranges from 0.01% to 20% by weight and preferably from 0.1% to 5% by weight relative to the weight of the composition.

The composition of the invention may be in various forms, for instance a solution, an emulsion (milk or cream) or a gel.

Processes of the Invention:

The composition used in the process according to the invention corresponds to the composition as defined previously and that is free of chemical oxidizing agent; this composition also being used in the presence of at least one chemical oxidizing agent.

This composition used in the process according to the invention (i.e. used in the presence of at least one chemical oxidizing agent) is applied to dry or wet keratin fibres.

It is usually left in place on the fibres for a time generally of from 1 minute to 1 hour and preferably from 5 minutes to 30 minutes.

The temperature during the dyeing process is conventionally between room temperature (between 15° C. and 25° C.) and 80° C. and preferably between room temperature and 60° C.

After the treatment, the human keratin fibres are advantageously rinsed with water. They may optionally be washed with a shampoo, followed by rinsing with water, before being dried or left to dry.

The composition applied in the process according to the invention (i.e. used in the presence of at least one chemical oxidizing agent) is generally prepared by mixing at least two compositions, preferably two or three compositions.

In a first variant of the invention, the composition applied in the process according to the invention (thus used with at least one chemical oxidizing agent) results from the mixing of two compositions.

In particular, a composition (A) (that does not comprise any chemical oxidizing agent) comprising at least one oxidation base, at least one coupler of formula (B3) and at least one alkalinizing agent is mixed with a composition (B) comprising at least one chemical oxidizing agent; at least one of the compositions (A) and (B) comprising at least one fatty substance, at least one surfactant, the fatty substance content of the composition applied in the process according to the invention, resulting from the mixing of compositions (A) and (B), comprising at least 25% by weight of fatty substance.

At least one of the compositions (A) and (B) is advantageously aqueous.

The expression "aqueous composition" means a composition comprising at least 5% by weight of water, relative to the weight of this composition.

Preferably, an aqueous composition comprises more than 10% by weight of water and more advantageously still more than 20% by weight of water.

Preferably, composition (A) is aqueous. Preferably, composition B is also aqueous.

In this variant, composition (A) preferably comprises at least 50% by weight of fatty substances, and more preferably still at least 50% by weight of fatty substances that are liquid at room temperature (25° C.), relative to the weight of this composition (A).

Preferably, composition (A) is a direct emulsion (oil-in-water: O/W) or an inverse emulsion (water-in-oil: W/O), and preferably a direct emulsion (O/W).

In this variant, compositions (A) and (B) are preferably mixed together in a weight ratio (A)/(B) ranging from 0.2 to 10 and better still from 0.5 to 2.

In a second variant of the invention, the composition used in the process according to the invention (thus in the presence of at least one chemical oxidizing agent) results from the mixing of three compositions. In particular, the three compositions are aqueous or alternatively at least one of them is anhydrous.

More particularly, for the purposes of the invention, the expression "anhydrous cosmetic composition" means a cosmetic composition with a water content of less than 5% by weight, preferably less than 2% by weight and more preferably still less than 1% by weight relative to the weight of said composition. It should be noted that the water present in the composition is more particularly "bound water", such as water of crystallization in salts, or traces of water absorbed by the raw materials used in the preparation of the compositions according to the invention.

Preferably, use is made of two aqueous compositions (B') and (C') and one anhydrous composition (A').

The anhydrous composition (A') (free of chemical oxidizing agent) then preferably comprises at least one fatty substance, and more preferably at least one liquid fatty substance.

Composition (B') (free of chemical oxidizing agent) then preferably comprises at least one oxidation base and at least one coupler of formula (B3).

Composition (C') then preferably comprises at least one chemical oxidizing agent.

According to this preferred embodiment of the second variant, the alkalinizing agent(s) may be included in compositions (A') and/or (B') and preferably only in composition (B').

As regards the surfactant(s), it is (they are) preferably included in at least one of compositions (A'), (B') and (C').

According to this preferred embodiment, the composition used in the process according to the invention, i.e. the composition resulting from the mixing of the three compositions (A'), (B') and (C'), has a fatty substance content of at least 25% by weight of fatty substance, relative to the weight of the composition resulting from the mixing of the three abovementioned compositions.

In this variant, compositions (A'), (B') and (C') are preferably mixed together in a weight ratio [(A14-(B')]/(C') ranging from 0.2 to 10 and more particularly from 0.5 to 2 and in a weight ratio (A')/(B') ranging from 0.5 to 10 and preferably from 1 to 5.

Devices:

Finally, the invention relates to a first multicompartment device comprising a first compartment containing composition (A) as described above and at least a second compartment containing composition (B) as described above; the compositions (A) and (B) of the compartments being intended to be mixed together before application to give a composition according to the invention; the amount of fatty substance of which represents at least 25% by weight relative to the weight of the formulation resulting from the mixing of compositions (A) and (B).

The invention also relates to a second multicompartment device comprising a first compartment containing composition (A') as described above and a second compartment containing a cosmetic composition (B') as described above and at least a third compartment comprising composition (C') as described above, the compositions of the compartments being intended to be mixed together before application to give the composition according to the invention; the amount of fatty substance in the composition representing at least 25% by weight relative to the weight of the composition of the invention, i.e. resulting from the mixing of compositions (A'), (B') and (C').

The examples that follow serve to illustrate the invention without, however, being limiting in nature.

EXAMPLES

The following compositions are prepared in which the amounts are expressed in grams of active materials.

| Composition A | |
|---|---|
| Liquid petroleum jelly | 64.5 |
| 2-Octyldodecanol | 11.5 |
| Distearyldimethylammonium-modified hectorite | 3 |
| Propylene carbonate | 1 |
| Oxyethylenated sorbitan monolaurate (4 EO) | 11 |
| Glycol distearate | 8 |
| Oxyethylenated lauryl alcohol (2 EO) | 1 |

| Composition B | |
|---|---|
| Propylene glycol | 6.2 |
| Ethyl alcohol | 8.25 |
| Hexylene glycol (2-methyl-2,4-pentanediol) | 3 |
| Dipropylene glycol | 3 |
| Monoethanolamine | 14.5 |
| Sodium metabisulphite | 0.7 |
| Vitamin C: L-ascorbic acid | 0.25 |
| Diethylenetriaminepentaacetic acid, pentasodium salt as a 40% aqueous solution | 1 |

-continued

| Composition B | |
|---|---|
| Hydroxyethyl cellulose (Natrosol 250 HHR, Aqualon) | 3.5 |
| Oxidation base | $2 \times 10^{-2}$ mol |
| Coupler | $2 \times 10^{-2}$ mol |
| Water | qs 100 g |

| Composition C1 (oxidizing agent) | |
|---|---|
| Cetylstearyl alcohol (Nafol 1618F) | 8 |
| Glycerol | 0.5 |
| Liquid petroleum jelly | 20 |
| Oxyethylenated cetylstearyl alcohol (33 EO) | 3 |
| Oxyethylenated rapeseed acid amide (4 EO) | 1.2 |
| Tetrasodium pyrophosphate | 0.03 |
| Diethylenetriaminepentaacetic acid, pentasodium salt as a 40% aqueous solution | 0.15 |
| Phosphoric acid | 0.1 |
| Tetramethylhexamethylenediamine/1,3-dichloropropylene polycondensate (40% aqueous solution) | 0.1 |
| Polydimethyldiallylammonium chloride (40% aqueous solution) | 0.2 |
| Hydrogen peroxide as a 50% aqueous solution | 6 |
| Sodium stannate | 0.04 |
| Vitamin E | 0.1 |
| Phosphoric acid | qs pH 2.2 |
| Water | qs 100 g |

At the time of use, the following are mixed together (by weight):

parts of composition A 4 parts of composition B 16 parts of composition C

The mixture obtained is then applied to locks of natural hair containing 90% grey hairs.

The "mixture/lock" bath ratio is respectively 10/1 (g/g).

The leave-on time is 30 minutes at 27° C.

After this time, the locks are rinsed, and then washed with shampoo and dried.

The results obtained with the composition of the invention were compared with those obtained with a composition from the prior art (Recital®) containing, in the mixture with the oxidizing agent, the same dyes at the same concentrations.

Calculation of the Colour Variation ($\Delta E_{ab}^*$)

The colour uptake ($\Delta E_{ab}^*$) was evaluated in the CIE L* a* b* system. In this L*, a*, b* system, L* represents the intensity of the colour, a* indicates the green/red colour axis and b* the blue/yellow colour axis. The lower the value of L*, the darker or more intense the colour.

The value of $\Delta E_{ab}^*$ was calculated from the values of L*a*b* according to equation (i) below:

$$\Delta E_{ab}^* = \sqrt{(L^*-L_o^*)^2+(a^*-a_o^*)^2+(b^*-b_o^*)^2} \quad (i)$$

The colour uptake ($\Delta E_{Lab}^*$) was calculated on locks of untreated hair ($L_o^*$, $a_o^*$ and $b_o^*$) and on locks of dyed hair (L*, a* and b*). The L*, a*, b* values for the untreated Natural Grey (NG) hair are as follows L*=57.93, a*=0.76, b*=14.32.

The greater the value of $\Delta E_{ab}^*$, the better the coverage of the treated fibres and thus of the roots.

Calculation of the Light Fastness machine: SUNTEST XLS+ (from Atlas) equipped with an infrared quartz filter and a special UV filter, xenon arc lamp (2200 W)

principle: the locks are fixed onto card supports, one half of the lock being obscured with a card. The sample holders are placed in the machine on horizontal plates arranged under the lamp, for 18 hours.

The light fastness is evaluated by determining the $DE_{light}^*$.

The value of $DE_{light}^*$ was calculated from the values of L*a*b* according to the equation:

$$DE_{light}^* = \Delta E_{ab}^* \text{ non-irradiated lock} - \Delta E_{ab}^* \text{ irradiated lock}$$

The lower the value of $DE_{light}$, the better the light fastness.

Results

| Base | Coupler | L* | a* | b* | $\Delta E_{ab}^*$ |
|---|---|---|---|---|---|
| 4-(3-aminopyrazolo[1,5-a]pyrid-2-yl)-1,1-dimethylpiperazin-1-ium hydrochloride | 3,5-dimethoxyphenol | 17.58 | −2.4 | −11.21 | 47.86 |
| 1-hydroxyethyl-4,5-diaminopyrazole sulphate | 3,5-dimethoxyphenol | 30.66 | 34.09 | 21.71 | 43.69 |

A high uptake on natural grey hair is observed, resulting in excellent coverage at the roots.

| Base | Coupler | SUNTEST (h) | L*(D65) | a*(D65) | b*(D65) | $\Delta E_{ab}^*$ | $DE_{lum}^*$ |
|---|---|---|---|---|---|---|---|
| 2-[(3-aminopyrazolo[1,5-a]pyrid-2-yl)oxy]ethanol hydrochloride | 3-methoxy-5-methylphenol | 0 | 16.46 | 4.03 | −12.39 | 49.44 | 0.38 |
| | | 18 | 16.68 | 3.31 | −12.12 | 49.06 | |
| 1-hydroxyethyl-4,5-diaminopyrazole sulphate | 3-methoxy-5-methylphenol | 0 | 23.07 | 28.59 | 14.28 | 44.61 | 0.3 |
| | | 18 | 24.22 | 30.37 | 16.21 | 44.91 | |
| 4-(3-aminopyrazolo-[1,5-a]pyrid-2-yl)-1,1-dimethyl-piperazin-1-ium chloride hydrochloride | 3,5-dimethoxy-phenol | 0 | 17.58 | −2.4 | −11.21 | 47.86 | 2.64 |
| | | 18 | 20.47 | −3.09 | −10.72 | 45.22 | |

It is observed that the colourings obtained have a very good light fastness.

The invention claimed is:

1. A composition for dyeing keratin fibers comprising a mixture of:
    composition (A) comprising:
        at least one surfactant,
        at least one alkalinizing agent,
        at least one fatty substance,
        at least one thickener,
        at least one oxidation base, and
        at least one coupler of formula (B3):

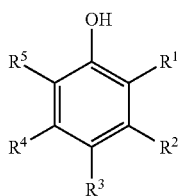

(B3)

and also salts thereof, optical and geometrical isomers and tautomers thereof, and hydrates thereof, wherein:

$R^1$, $R^3$, and $R^5$, which may be identical or different, are chosen from:
  hydrogen;
  optionally substituted, linear or branched $C_1$-$C_8$ alkyl and $C_3$-$C_8$ alkenyl radicals;
  —SR and —OR groups in which R is chosen from hydrogen and optionally substituted, linear or branched $C_1$-$C_8$ alkyl and $C_3$-$C_8$ alkenyl radicals;
  $(C_1$-$C_4)$alkylcarbonyl groups;
  hydrocarbonyl groups (HCO—);
  sulphonic acid groups; and
  carboxylic acid group;

$R^2$ and $R^4$, which may be identical or different, are chosen from:
  hydrogen;
  optionally substituted, linear or branched $C_1$-$C_8$ alkyl and $C_3$-$C_8$ alkenyl radicals; and
  —OR' groups in which R' is chosen from optionally substituted, linear or branched $C_1$-$C_8$ alkyl and $C_3$-$C_8$ alkenyl radicals;

two groups chosen from $R^1$, $R^2$, $R^3$, $R^4$, and $R^5$ and borne by adjacent carbon atoms may form, together with said carbon atoms, a ring or a heterocycle, optionally comprising from one to three heteroatoms, optionally substituted, and optionally interrupted with at least one carbonyl group; and at least one of the radicals $R^1$, $R^3$, and $R^5$ is a hydrogen atom and at least one of the radicals $R^2$ and $R^4$ are chosen from —OR' groups in which R' is chosen from optionally substituted, linear or branched $C_1$-$C_8$ alkyl and $C_3$-$C_8$ alkenyl radicals, it being possible for this radical to form, with the carbon atom bearing it, one of the neighboring carbon atoms and its substituent, a heterocycle optionally comprising from one to three heteroatoms, optionally substituted, and optionally interrupted with at least one carbonyl group;

composition (B) comprising:
    at least one chemical oxidizing agent,
    wherein the amount of fatty substance in composition (A) is least about 50% by weight relative to the total weight of composition (A), and
    wherein the at least one fatty substance is present in the mixture of compositions (A) and (B) in a total amount of at least about 25% by weight relative to the total weight of the mixture.

2. The composition according to claim 1, wherein the at least one fatty substance is chosen from $C_6$-$C_{16}$ alkanes, non-silicone oils of mineral, plant, animal or synthetic origin, fatty alcohols, fatty acid esters, fatty alcohol esters, non-silicone waxes and silicones.

3. The composition according to claim 2, wherein the at least one fatty substance is liquid at room temperature and at atmospheric pressure.

4. The composition according to claim 2, wherein the at least one fatty substance is chosen from liquid petroleum jelly, $C_6$-$C_{16}$ alkanes, polydecenes, and esters of fatty acids or of fatty alcohols, which are liquid, and mixtures thereof.

5. The composition according to claim 2, wherein the at least one fatty substance is present in the mixture in an amount ranging from about 25% to about 80% by weight relative to the total weight of the mixture.

6. The composition according to claim 1, wherein the at least one surfactant is chosen from nonionic surfactants.

7. The composition according to claim 1, wherein the at least one surfactant is chosen from monooxyalkylenated or polyoxyalkylenated, monoglycerolated or polyglycerolated surfactants.

8. The composition according to claim 1, wherein the at least one heterocyclic base is chosen from pyridine derivatives, pyrimidine derivatives and pyrazole derivatives, and the addition salts thereof.

9. The composition according to claim 1, wherein the at least one coupler of formula (B3) is chosen from those in which:
    $R^1$, $R^3$, and $R^5$, which may be identical or different, are chosen from:
        hydrogen;
        linear or branched $C_1$-$C_8$ alkyl and $C_3$-$C_8$ alkenyl radicals, optionally substituted with at least one group chosen from hydroxyl, amino and carboxyl groups;
        —OR groups in which R is chosen from hydrogen and linear or branched $C_1$-$C_4$ alkyl radicals;
        ($C_1$-$C_4$)alkylcarbonyl groups; and
        carboxylic acid groups;
    $R^2$ and $R^4$, which may be identical or different, are chosen from:
        hydrogen;
        linear or branched $C_1$-$C_4$ alkyl radicals; and
        —OR' groups in which R' is chosen from linear or branched $C_1$-$C_8$ alkyl radicals;
    two groups chosen from $R^1$, $R^2$, $R^3$, $R^4$, and $R^5$ and borne by adjacent carbon atoms may form, together with said carbon atoms, a heterocycle comprising 5 or 6 ring members, comprising one or two identical or different heteroatoms chosen from oxygen and sulphur atoms, optionally interrupted with at least one carbonyl group and optionally substituted with at least one $C_1$-$C_4$ alkyl radical; and
    at least one of the radicals $R^1$, $R^3$, and $R^5$ is a hydrogen atom and at least one of the radicals $R^2$ or $R^4$ is chosen from —OR' groups in which R' is chosen from optionally substituted, linear or branched $C_1$-$C_8$ alkyl and $C_3$-$C_8$ alkenyl radicals, it being possible for this radical to form, with the carbon atom bearing it, one of the neighboring carbon atoms and its substituent, a heterocycle optionally comprising from one to three heteroatoms, optionally substituted, and optionally interrupted with at least one carbonyl group.

10. The composition according to claim 1, wherein the at least one coupler of formula (B3) is chosen from those in which:
    $R^1$, $R^3$, and $R^5$, which may be identical or different, are chosen from:
        hydrogen;
        linear or branched $C_1$-$C_6$ alkyl radicals;
        —OR groups in which R is chosen from hydrogen and linear or branched $C_1$-$C_4$ alkyl radicals;
        ($C_1$-$C_4$)alkylcarbonyl groups; and
        carboxylic acid groups;
    $R^2$ and $R^4$, which may be identical or different, are chosen from:
        hydrogen;
        linear or branched $C_1$-$C_4$ alkyl radicals; and
        —OR' groups in which R' is chosen from linear or branched $C_1$-$C_8$ alkyl radicals;
    two groups chosen, on the one hand, from $R^1$ and $R^2$ and, on the other hand, from $R^4$ and $R^5$ may form, together with the carbon atoms to which they are attached, a heterocycle comprising 5 or 6 ring members, comprising one or two oxygen atoms, optionally interrupted with at least one carbonyl group and optionally substituted with at least one $C_1$-$C_4$ alkyl radical;
    at least one of the radicals $R^1$, $R^3$, and $R^5$ is a hydrogen atom and at least one of the radicals $R^2$ and $R^4$ is chosen from —OR' groups in which R' is chosen from optionally substituted, linear or branched $C_1$-$C_8$ alkyl and $C_3$-$C_8$ alkenyl radicals, it being possible for this radical to form, with the carbon atom bearing it, one of the neighboring carbon atoms and its substituent, a heterocycle optionally comprising from one to three heteroatoms, optionally substituted, and optionally interrupted with at least one carbonyl groups.

11. The composition according to claim 1, wherein the at least one coupler of formula (B3) is chosen from the following compounds, and salts thereof, optical and geometrical isomers and tautomers thereof, and hydrates thereof:

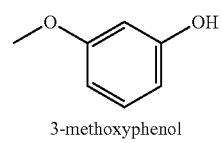

150-19-6

3-methoxyphenol

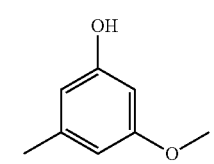

3209-13-0

3-methoxy-5-methylphenol

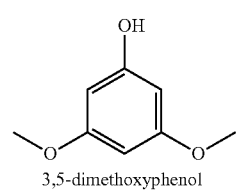

500-99-2

3,5-dimethoxyphenol

-continued

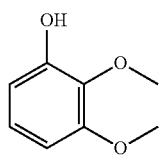
2,3-dimethoxyphenol

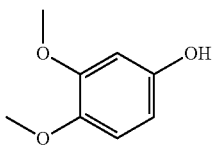
3,4-dimethoxyphenol

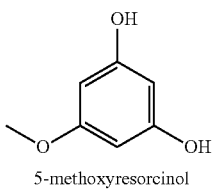
5-methoxyresorcinol

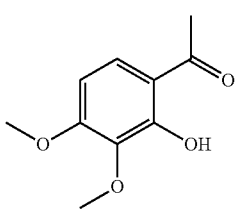
3′,4′-dimethoxy-2′-hydroxyacetophenone

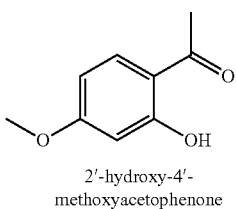
2′-hydroxy-4′-methoxyacetophenone

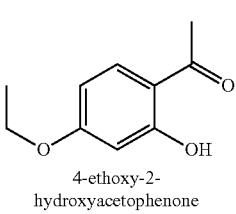
4-ethoxy-2-hydroxyacetophenone

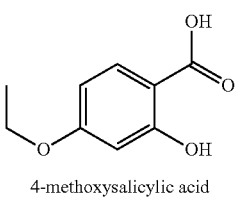
4-methoxysalicylic acid

-continued 5150-42-5

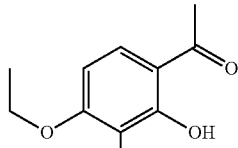
4′-ethoxy-2′-hydroxy-3′-ethylacetophenone
536723-94-1

2033-89-8

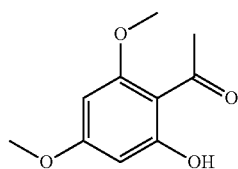
2′-hydroxy-4′,6′-dimethoxyacetophenone
90-24-4

2174-64-3

5396-18-9

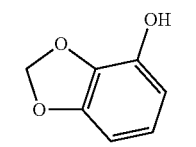
benzo[d][1,3]dioxol-4-ol
69393-72-2

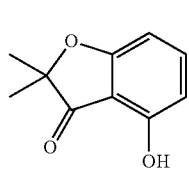
4-hydroxy-2,2-dimethyl-benzofuran-3-one
81407-92-3

552-41-0

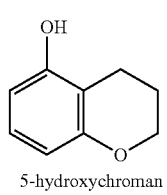
5-hydroxychroman
942-56-3

37470-42-1

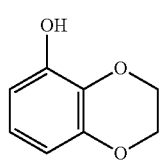
2,3-dihydro-1,4-benzodioxin-5-ol
10288-36-5

2237-36-7

12. The composition according to claim 1, wherein the at least one coupler of formula (B3) is chosen from the following compounds, and salts thereof, optical and geometrical isomers and tautomers thereof, and hydrates thereof:

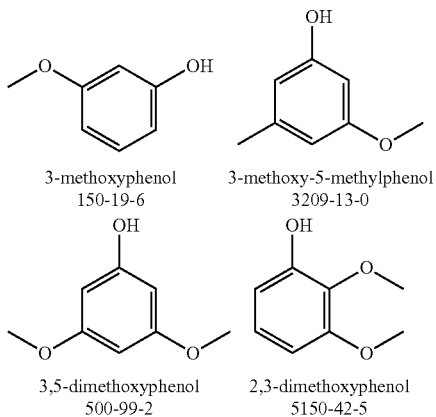

3-methoxyphenol 150-19-6
3-methoxy-5-methylphenol 3209-13-0
3,5-dimethoxyphenol 500-99-2
2,3-dimethoxyphenol 5150-42-5

13. The composition according to claim 1, wherein the at least one alkalinizing agent is chosen from mineral, organic and hybrid compounds.

14. The composition according to claim 1, wherein the at least one alkalinizing agent is chosen from aqueous ammonia; alkali metal carbonates or bicarbonates; sodium carbonate or bicarbonate; potassium carbonate or bicarbonate; sodium hydroxide; potassium hydroxide; organic amines chosen from alkanolamines; oxyethylenated and/or oxypropylenated ethylenediamines; amino acids and the compounds of formula (I); and mixtures thereof:

(I)

wherein W is chosen from $C_1$-$C_6$ divalent alkylene radicals optionally substituted with at least one entity chosen from hydroxyl groups and $C_1$-$C_6$ alkyl radicals, and/or optionally interrupted with at least one heteroatom chosen from O and $NR_u$; and $R_x$, $R_y$, $R_z$, $R_t$ and $R_u$, which may be identical or different, are chosen from hydrogen and $C_1$-$C_6$ alkyl and $C_1$-$C_6$ hydroxyalkyl radicals and $C_1$-$C_6$ aminoalkyl radicals.

15. The composition according to claim 1, wherein the at least one alkalinizing agent is chosen from alkanolamines and amino acids in neutral or ionic form.

16. The composition according to claim 1, wherein the at least one chemical oxidizing agent is hydrogen peroxide.

17. A process for dyeing keratin fibers comprising applying to the fibers, a composition for dyeing keratin fibers according to claim 1.

18. A multi-compartment device comprising a first compartment containing composition (A) as described in claim 1 and at least a second compartment containing composition (B) as described in claim 1, the compositions of the compartments being intended to be mixed together before application.

* * * * *